United States Patent
Prochiantz et al.

(10) Patent No.: US 10,100,307 B2
(45) Date of Patent: Oct. 16, 2018

(54) USE OF A REVERSE-TRANSCRIPTASE INHIBITOR IN THE PREVENTION AND TREATMENT OF DEGENERATIVE DISEASES

(71) Applicants: Centre National de la Recherche Scientifique, Paris (FR); College de France, Paris (FR); Institut National de la Sante et de la Recherche Medicale (INSERM), Paris (FR); Sorbonne Universite, Paris (FR)

(72) Inventors: Alain Prochiantz, Paris (FR); Julia Fuchs, Pantin (FR); Rajiv Joshi, Massy (FR); François Xavier Blaudin De The, Paris (FR); Hocine Rekaik, Melun (FR); Olivia Massiani-Beaudoin, Montgeron (FR)

(73) Assignees: Centre National de la Recherche Scientifique, Paris (FR); Institut National de la Sante et de la Recherche Medicale (INSERM), Paris (FR); College de France, Paris (FR); Sorbonne Universite, Paris (FR)

( * ) Notice: Subject to any disclaimer, the term of this patent is extended or adjusted under 35 U.S.C. 154(b) by 0 days.

(21) Appl. No.: 15/520,926

(22) PCT Filed: Oct. 30, 2015

(86) PCT No.: PCT/IB2015/058404
§ 371 (c)(1),
(2) Date: Apr. 21, 2017

(87) PCT Pub. No.: WO2016/067265
PCT Pub. Date: May 6, 2016

(65) Prior Publication Data
US 2017/0335320 A1 Nov. 23, 2017

(30) Foreign Application Priority Data
Oct. 31, 2014 (FR) ..................... 14 60535

(51) Int. Cl.
*C12N 15/113* (2010.01)
*C12Q 1/68* (2018.01)
*C12N 15/63* (2006.01)
*C12Q 1/25* (2006.01)

(52) U.S. Cl.
CPC .......... *C12N 15/113* (2013.01); *C12N 15/63* (2013.01); *C12Q 1/25* (2013.01); *C12Q 1/68* (2013.01); *C12N 2740/00011* (2013.01)

(58) Field of Classification Search
None
See application file for complete search history.

(56) References Cited

U.S. PATENT DOCUMENTS

2015/0018297 A1 1/2015 Jo et al.

FOREIGN PATENT DOCUMENTS

| DE | 4307883 A1 | 9/1993 | |
|---|---|---|---|
| KR | 2010-0073528 A | 7/2010 | |
| WO | 00/50043 A1 | 8/2000 | |
| WO | 2009/153009 A1 | 12/2009 | |
| WO | WO-2016138425 A1 * | 9/2016 | .......... C07D 405/04 |

OTHER PUBLICATIONS

Ahn et al., "Inhibition of HIV-1 reverse transcriptase and protease by phlorotannins from the brown alga Ecklonia cava," Biological & Pharmaceutical Bulletin, 27: 544-547 (2004).
Chu et al., "Inhibitory effects of flavonoids on Moloney murine leukemia virus reverse transcriptase activity," Journal of Natural Products, 55: 179-183 (1992).
Westarp et al., "Antiretroviral therapy in sporadic adult amytrophic lateral sclerosis," NeuroReport 4: 819-822 (1993).
Westarp et al., "Amyotrophic Lateral Sclerosis an Enigmatic Disease with B-Cellular and Anti-Retroviral Immune Response," European Journal of Medicine, 2: 327-332 (1993).
International Search Report issued in corresponding International Patent Application No. PCT/IB2015/058404 dated Feb. 24, 2016.

\* cited by examiner

*Primary Examiner* — Sean McGarry
(74) *Attorney, Agent, or Firm* — Morgan, Lewis & Bockius LLP

(57) ABSTRACT

The invention relates to the use of a reverse-transcriptase inhibitor in the prevention or treatment of a degenerative disease.

Figure 1:
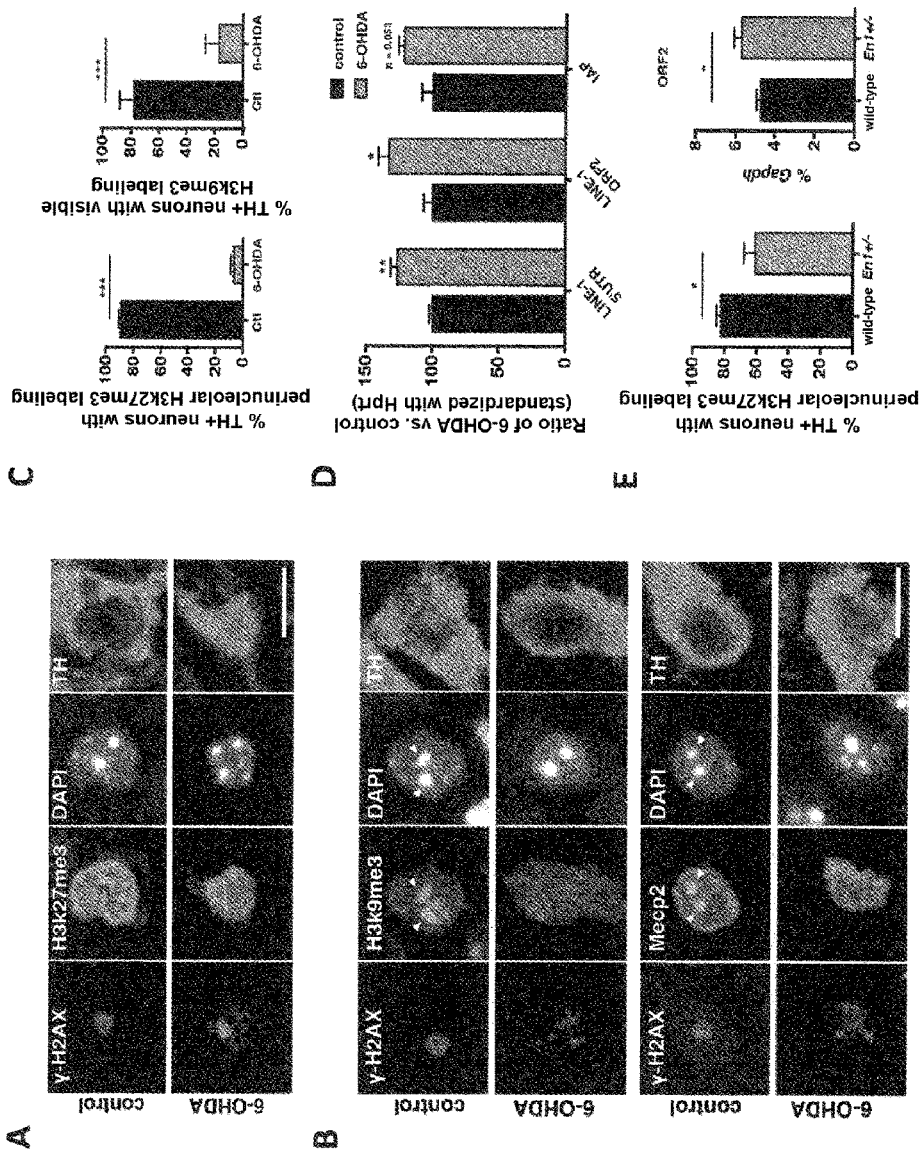

9 Claims, 3 Drawing Sheets
Specification includes a Sequence Listing.

USE OF A REVERSE-TRANSCRIPTASE INHIBITOR IN THE PREVENTION AND TREATMENT OF DEGENERATIVE DISEASES

SEQUENCE LISTING SUBMISSION VIA EFS-WEB

A computer readable text file, entitled "SequenceListing.txt," created on or about 12 Apr. 2017 with a file size of about 2 kb contains the sequence listing for this application and is hereby incorporated by reference in its entirety.

The present invention relates to the use of a reverse transcriptase inhibitor in the prevention and treatment of degenerative diseases.

A characteristic of most degenerative diseases, in particular neurodegenerative diseases, is that they manifest late in life. This is true of both their sporadic and genetic forms, as is illustrated by Parkinson's disease, Alzheimer's disease and even the monogenetic Huntington's disease. This suggests that aging makes the cells more sensitive, even if the mutations themselves accelerating this aging cannot be ruled out.

Oxidative stress, which mimics accelerated aging, generates reactive oxygen species (ROS) which are toxic, in particular in terms of the genome, where the chromatin proteins and the DNA bases are subjected to oxidation (Vijg, J., and Suh, Y., 2013). Reactive oxygen species may induce single-stranded and double-stranded (DSB) DNA breaks, thereby activating DNA damage response systems (O'Sullivan and Karlseder, 2012; Marteijn et al., 2014). For example, a recent article shows that, in mice, neuronal activity and hence the synthesis of ATP and reactive oxygen species are accompanied physiologically by the formation of double-stranded DNA breaks, which are rapidly repaired in wild-type mice, unlike in J20 mice, which are an Alzheimer's disease model (Suberbielle et al., 2013).

Long interspersed nuclear elements (LINEs) form part of the repeat sequences spread throughout DNA. Active LINE sequences are non-long terminal repeat (LTR) transposable elements capable of autonomous replication, which enables them to duplicate themselves and insert themselves into other sites in the genome. LINEs encode a polycistronic RNA with two open reading frames, ORF1 and ORF2. ORF2 encodes a reverse transcriptase (RT) which copies the LINE RNA into DNA and an endonuclease which enables the insertion of this DNA into the genome via the formation of a double-stranded break, and which at the same time introduces a mutation into the genome which may prove deleterious.

The inventors have shown that oxidative stress which mimics accelerated aging induces the formation of double-stranded DNA breaks (DSB), destructuring of the heterochromatin and expression of genes of transposable elements (LINEs). They have proposed that the expression of LINEs induced by oxidative stress is the basis, at least partially, of DSB formation, and demonstrated that the formation of these DSBs is reduced in the presence of a reverse transcriptase inhibitor.

On the basis of these observations, the inventors propose to use reverse transcriptase inhibitors in the prevention and treatment of degenerative diseases.

Consequently, the subject of the present invention is a reverse transcriptase inhibitor, for use thereof in the prevention and/or treatment of a degenerative disease.

In accordance with the invention, the degenerative disease is a disease of genetic and/or acquired origin, especially linked to age (aging) and/or to stress, especially to oxidative stress.

Due to the fact that it reduces the formation of DSBs, the reverse transcriptase inhibitor has a therapeutic effect in degenerations linked to age and/or to stress, or indeed to conditions which increase the deleterious effects of the stress (a mutation, for example).

It is useful, especially in the prevention and treatment of neurodegenerative diseases, in particular late-onset neurodegenerative diseases, of neuronal aging, and of the effects of oxidative stress in nerve cells or other types of cells.

Among the degenerative diseases, mention may be made, nonlimitingly, of neurodegenerative diseases such as, for example, Parkinson's disease, Alzheimer's disease, Huntington's disease, amyotrophic lateral sclerosis (ALS), and degenerative diseases affecting eyesight or hearing, especially glaucoma.

The reverse transcriptase inhibitor is a specific inhibitor of reverse transcriptase. The reverse transcriptase inhibitor is a nucleoside inhibitor or non-nucleoside inhibitor.

Among the inhibitors which may be used in the context of the present invention, mention may especially be made of those currently available as medicament in the treatment of human immunodeficiency virus (HIV) infection, namely nucleoside inhibitors such as: azidothymidine (AZT or Zidovudine or), 2'-3'-dideoxycytidine (ddC or Zalcitabine), [(1R)-4-[2-amino-6-(cyclopropylamino)purin-9-yl]-1-cyclopent-2-enyl]methanol (ABC or Abacavir), 2'-3'-didehydro-2'-3'-dideoxythymidine (d4T or Stavudine), 2',3'-dideoxy-3'-thiacytidine (3TC or Lamivudine), ddI (2'-3'-dideoxyinosine), 4-amino-5-fluoro-1-[2-(hydroxymethyl)-1,3-oxathiolan-5-yl]-pyrimidin-2-one (FTC), 2-(6-aminopurin-9-yl)ethoxymethyl-phosphonic acid (bis-POM PMPA), Adefovir, Didanosine, Emtricitabine and Tenofovir; non-nucleoside inhibitors such as Efavirenz (EFV), Nevirapine (NVP), Delavirdine (DLV), Etravirine and Rilvipirine.

According to an advantageous embodiment of the invention, said inhibitor is a nucleoside inhibitor, preferably Stavudine.

The inhibitor is administered via a route adapted to the pathological condition to be treated (orally, parenterally, locally) and at sufficient doses to obtain the desired therapeutic effect, which may be readily determined by those skilled in the art.

Aside from the preceding provisions, the invention comprises other provisions which will emerge from the following description, which refers to exemplary embodiments of the present invention.

EXAMPLE 1

Oxidative Stress Induces the Formation of Double-Stranded Breaks (DSBs), Destructuring of the Heterochromatin and Expression of Genes of Transposable Elements (LINEs)

1. Material and Methods

Animals

The mice were treated in accordance with the directives for keeping and using laboratory animals of the National Institutes of Health (United States) and European Directive 86/609/EEC for the protection of animals used for experimental and other scientific purposes. Wild-type Swiss OF1 mice (Janvier) or heterozygous $En1^{+/-}$ mutants (Hanks et al., 1995) were kept in conventional animal houses. The experimental groups consist of mice aged from 6 to 9 weeks.

6-OHDA Treatment

For the 6-OHDA (6-hydroxydopamine) injections, anesthetized mice were placed on a stereotactic device and a burr hole was drilled in the cranium, 3.3 mm caudally and 1 mm laterally from the bregma. The needle of the syringe was aligned over the hole and descended 4 mm from the surface of the cranium, and 6-OHDA (2 µl; 0.8 µg/µl Sigma) or control (NaCl 0.9%) was injected into the SNpc for more than 4 min. For the immunohistological analysis, the mice were sacrificed 6 h, 24 h or 7 days after 6-OHDA injection. For the qRT-PCR analyses, tissues from the SNpc 6 h after 6-OHDA injection were obtained by extracting 1 mm samples from 2 mm thick disks of frozen tissue, using a stereotactic apparatus.

qRT-PCR

The total RNA from the SNpc tissue was extracted using the RNeasy® Lipid Tissue kit (Qiagen) followed by DNase I (Thermo) digestion, then reverse transcription was carried out on 200 ng of RNA using the Sensiscript® or QuantiTect Reverse Transcription (Qiagen) kit. qRT-PCR reactions were carried out with specific primer pairs for the sequences to be amplified, using the SYBR-Green (Invitrogen or Roche Applied Science) kit and a LightCycler® 480 thermal cycler, and the values were standardized relative to the content of Gadph and/or Hprt mRNA. The results were analyzed using the ddCt method (Livak and Schmittgen, 2001).

Immunolabeling

The mice were anesthetized then a transcardial perfusion was carried out with PBS, then PBS containing 4% paraformaldehyde. The brains were post-fixed for 1 h and cryoprotected with a 20% sucrose solution.

The tissues were embedded in OCT, frozen in cooled isopentane, then preserved at −80° C. before being sectioned. 20 µm thick sections of the brain at the SNpc were made. For the immunofluorescence, the slices were air-dried, permeabilized for 20 min in PBS containing 1% Triton X-100 and incubated at 100° C. for 20 min in citrate buffer (10 mM citric acid, 0.05% Tween 20, pH 6.0) to demask the antigen. After 1 h of blocking (10% normal goat serum, 0.05% Triton X-100 in PBS), the tissues were incubated overnight at 4° C. with primary antibodies diluted in the blocking solution (mouse anti-γ-H2AX, 1:200, Millipore; chicken anti-TH, 1:500, Abcam; rabbit anti-active caspase 3, 1:200, Abcam; rabbit anti-nucleolin, 1:200, Sigma; rabbit anti-fibrillarin, 1:200, Gentex; rabbit anti-H3k27me3, 1:200, Millipore; rabbit anti-H3k9me3, 1:200, Edith Heard; rabbit anti-Mecp2, 1:300, Abcam; rabbit anti-PCNA, 1:200, Cell Signaling; rabbit anti-cyclin A, 1:200, Santa Cruz; mouse anti-phospho-H3, 1:100, Cell Signaling; rabbit anti-Lamin, Santa Cruz; anti-LINE ORF1p, 1:500). The sections were incubated with the appropriate secondary antibodies (488 anti-chicken, 647 anti-chicken, 488 anti-mouse, 546 anti-mouse and 546 anti-rabbit, Alexa Fluor, Life Technologies) for 1 h at room temperature. The labeled brain sections were visualized using a confocal fluorescence microscope (SP5, Leica). For the TH immunohistochemistry, the slices were permeabilized in a solution of 1% Triton X-100 and incubated overnight at 4° C. with PBS, 10% normal goat serum containing a rabbit anti-TH polyclonal antibody (1:1000; Pel-Freez Biologicals). The sections were treated with a biotinylated secondary antibody (Vector Lab) then incubated with a biotinylated avidin-horseradish peroxidase (HRP) complex (ABC system, Vectastain). The peroxidase was revealed using the peroxidase (HRP) substrate kit based on diaminobenzidine (DAB) (Vector Lab) then visualized with an Eclipse i90 microscope (Nikon).

Quantification of the Images

The microscopy images were analyzed using the ImageJ software. For the immunofluorescence, all the quantifications were carried out using 60× enlargement and successive focal planes 0.7 µm in thickness. DAPI staining was used to localize the nuclei of the cells immunolabeled with TH. 100 to 300 individual TH-positive cells were quantified for each condition. For counting of the γ-H2AX foci, the number of γ-H2AX points in the nucleus of each cell was determined; due to endogenous labeling, a threshold of 2 foci per cell was established. For analysis of the H3K27me3 and Nucleolin motifs, a two-dimensional graph of the pixel intensity along a line passing through the nucleus was created. The specific motifs identified were used to determine the presence of H3K27me3. For analysis of the H3K9me3 and Mecp2 labeling, the same procedure was used with DAPI-dense chromocenters. The ratio of the perinuclear and nuclear H3k27me3 fluorescences was determined by measuring the pixel density along the nuclear envelope and the DAPI-stained nucleoplasm.

2. Results

Oxidative stress mimicking accelerated aging was induced specifically in midbrain dopaminergic (mDA) neurons of the substantia nigra pars compacta (SNpc) by local injection of an oxidizing drug, 6-OHDA (6-hydroxydopamine), captured via dopamine (DA) transporters expressed specifically by the mDA neurons of the SNpc.

Midbrain sections of mice injected with 6-OHDA and control mice were labeled with specific antibodies for γ-H2AX, H3K27me3 and tyrosine hydroxylase (TH; a marker of dopaminergic neurons) and analyzed by confocal fluorescence microscopy.

Six hours after injection of 6-OHDA into the substantia nigra pars compacta (SNpc) of the mice, a reduction in perinucleolar and perinuclear H3K27m3 labeling is observed in the TH+ neurons compared to the control mice (FIG. 1A).

The triple immunolabeling of the midbrain sections by γ-H2AX, H3K27me3 and TH shows that the colocalization of H3K27me3 with DAPI, observed in the TH+ neurons of the control mice, disappears in the mice injected with 6-OHDA (FIG. 1B).

Similarly, the colocalization of MeCP2 with DAPI, observed in the TH+ neurons of the control mice, disappears in the mice injected with 6-OHDA (FIG. 1B).

The percentage of TH+ neurons with perinucleolar H3K27me3 labeling or visible H3K9me3 is significantly reduced in the mice injected with 6-OHDA (n=3, ***p<0.001). The number of neurons counted for the control and 6-OHDA is, respectively, 148 and 91 for H3K27me3 and 161 and 97 for H3K9me3 (FIG. 1C).

The contents of LINE-1 and IAP (intracisternal A particle) transcripts in the SNpc, analyzed by qRT-PCR, are increased in the mice injected with 6-OHDA, compared to the control animals (n=3) (FIG. 1D).

Midbrain sections from En1$^{+/-}$ mice aged 9 weeks were analyzed for H3K27 labeling. The quantification showed a reduction in the percentage of TH+ neurons with dense perinucleolar H3K27 labeling compared to wild-type mice (wt) (FIG. 1E; n=3, *p<0.05, 125 and 162 neurons counted in wt and En1$^{+/-}$, respectively). The contents of LINE-1 ORF2 transcripts in the SNpc of En1$^{+/-}$ mice, analyzed by qRT-PCR, increase in comparison to the wild-type mice (FIG. 1E; n=3-5, *p<0.05 , **p<0.01).

6-OHDA kills neurons in 24 h via an apoptotic mechanism (expression of activated caspase 3) which involves the formation of double-stranded breaks in the DNA (histone mark H2AX phosphorylated at S140 (gamma-H2AX)), nucleolar stress (dissolution of nucleolin and fibrillarin) and destructuring of the heterochromatin (diffusion of H3K27me3, histone H3 trimethylated at lysine 27, a marker of heterochromatin), H3K9me3 (histone H3 trimethylated at lysine 9), MeCP2 (Methyl-CpG-binding protein 2) and lamin B2, as illustrated in FIGS. 1A, 1B and 1C.

The double-stranded DNA breaks and the destructuring of the heterochromatin are accompanied by expression of normally repressed genes (encoded in the heterochromatin), in particular genes encoding retrotransposons (including long interspersed nuclear elements or LINEs) and proteins of the cell cycle (cyclin A pH3 and PCNA), normally silent in these post-mitotic cells, as illustrated in FIG. 1D.

These phenotypes are observable to a lesser extent in an Engrailed $1^{+/-}$ (En1$^{+/-}$) mutant, the neurons of which die gradually (FIG. 1E).

Consequently, FIG. 1 shows that ROSs, or the loss of an allele of the gene Engrailed 1 (En1), relax the heterochromatin and lead to expression of LINEs.

EXAMPLE 2

Figure 2:
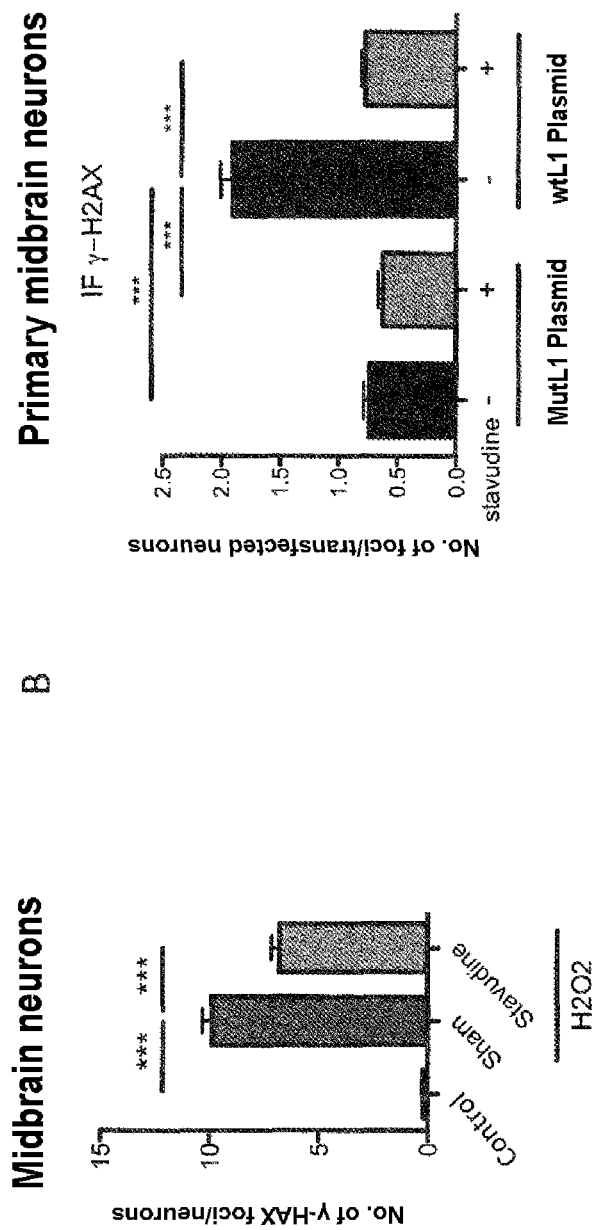

The Formation of DSBs Induced by Oxidative Stress is Reduced in the Presence of a Reverse Transcriptase Inhibitor 1. Material and Methods
In Vitro Assays
Cell Culture Embryonic midbrain neurons (embryonic day 13.5) are cultured in NBGK medium (Neurobasal® (Life Technologies) supplemented with glutamine (500 µM, SIGMA), glutamic acid (3.3 mg/ml, SIGMA), aspartic acid (3.7 mg/ml, SIGMA), anti-anti and B27® (GIBCO)). A midbrain neuron culture was incubated overnight in the presence of Stavudine (10 µM in 0.9% NaCl). A control culture was treated under the same conditions, with a solution of NaCl (0.9%). The following day, the culture medium was replaced with Neurobasal® medium (Life Technologies) not supplemented with B27® (Life Technologies), containing 5 µM of $H_2O_2$ and 10 µM Stavudine/NaCl, for 1 h (FIG. 2). Alternatively, the cells were treated with $H_2O_2$ (100 µM) in the presence of B27 for one hour. Stavudine (10 µM) was added twice, 24 hours before and during treatment with $H_2O_2$ or lipofection (FIG. 2). The neurons were then fixed with PBS 4% paraformaldehyde (PFA) for 20 min, then treated with glycine (100 mM) in PBS for 10 min. The cells were blocked in PBS containing 10% goat serum for 1 hour, then incubated overnight at room temperature with anti-S140 phosphorylated histone H2AX (gamma-H2AX) in PBS containing 3% goat serum and 0.1% Triton X-100, and 1 hour at room temperature with the secondary antibody coupled to a fluorophore. The number of gamma-H2AX foci per neuron was counted on several slides, then the mean was taken over more than 30 neurons. The results represent 4 independent experiments.

The transfection protocol was adapted from Dalby et al. (2004). The plasmids (0.75 µg per transfection) were pre-incubated with 8 µl of Lipofectamine® 2000 (Life Technologies) for 20 min at room temperature in Opti-MEM® medium (Life Technologies). The medium was added and the mixture was added to the cells for 48 h at 37° C., then immunofluorescence was carried out.

Reverse Transcription Assay

Normal HEK cells or those which are inducible by the Engrailed (En) protein were treated with doxycycline for one day to induce Engrailed expression. Next, the cells were transfected with a retrotransposition plasmid similar to that described in Xie et al., 2011, with just one mouse LINE-1 gene and a GFP cassette. The cells were divided one day after transfection, then treated with puromycin (0.7 µg/µl, Sigma) 3 days later in order to eliminate the non-transfected cells. After one week, the percentage of GFP-positive cells was measured by flow cytometry.

In Vivo Assays

Mice were treated with Stavudine (10 µM; SIGMA) followed 30 min later by the injection of a mixture containing 6-OHDA (2 µl; 0.5 µg/µl; Sigma) and Stavudine (10 µM; SIGMA) as indicated in Example 1. Immunolabeling was carried out as described in Example 1 then visualized with an Optiphot 2 microscope (Nikon). The microscopy images were analyzed using the VisioScan T4.18 software (ExploraNova, La Rochelle, France) as described previously (Höglinger et al. 2003). The cell numbers were quantified stereologically on sections spaced apart regularly covering all of the rostrocaudal extent of the substantia nigra, using the VisioScan stereology tool. The substantia nigra pars compacta (SNpc) was identified according to established anatomical markers (Paxinos mouse brain atlas). qRT-PCR analysis was carried out as described in Example 1, using the following primer pairs: the pair SEQ ID NO: 1 and 2 (LINE-1 Tf/Gf) and the pair SEQ ID NO: 3 and 4 (LINE-1A), specific to the gene LINE-1; the pair SEQ ID NO: 5 and 6, specific to the gene Hprt; the pair SEQ ID NO: 7 and 8, specific to the gene Gapdh.

2. Results

Mouse embryonic midbrain neurons (14 days' gestation), treated or untreated with an RT inhibitor (Stavudine), were subjected to an oxidative stress by addition of $H_2O_2$. This superoxide, unlike 6-OHDA, is not specific just to mDA neurons (which only make up 1.5% of the culture), but rather affects all cells. The number of DSBs per neuron was evaluated after γ-H2AX labeling.

The results presented in FIG. 2A show that $H_2O_2$ increases the number of DSBs in vitro. Nonetheless, the formation of DSBs is significantly reduced (40% reduction) by Stavudine, a reverse transcriptase inhibitor which reduces the formation of DNA breaks by LINE transcripts (***$p<0.001$; n=6, ANOVA test for a single factor, Bonferroni multiple comparisons test). FIG. 2A therefore shows that an RT inhibitor reduces the formation of DSBs induced by an oxidative stress in vitro.

Transfection with a plasmid (wt L1) overexpressing the gene LINE-1 in primary midbrain neurons induces the formation of DNA breaks (FIG. 2B). This effect is suppressed by Stavudine (FIG. 2B) or a plasmid (Mut L1) in which the ORF2 of the gene LINE-1 is mutated (***$p<0.001$; n=6, ANOVA test for a single factor, Bonferroni multiple comparisons test).

Figure 3:
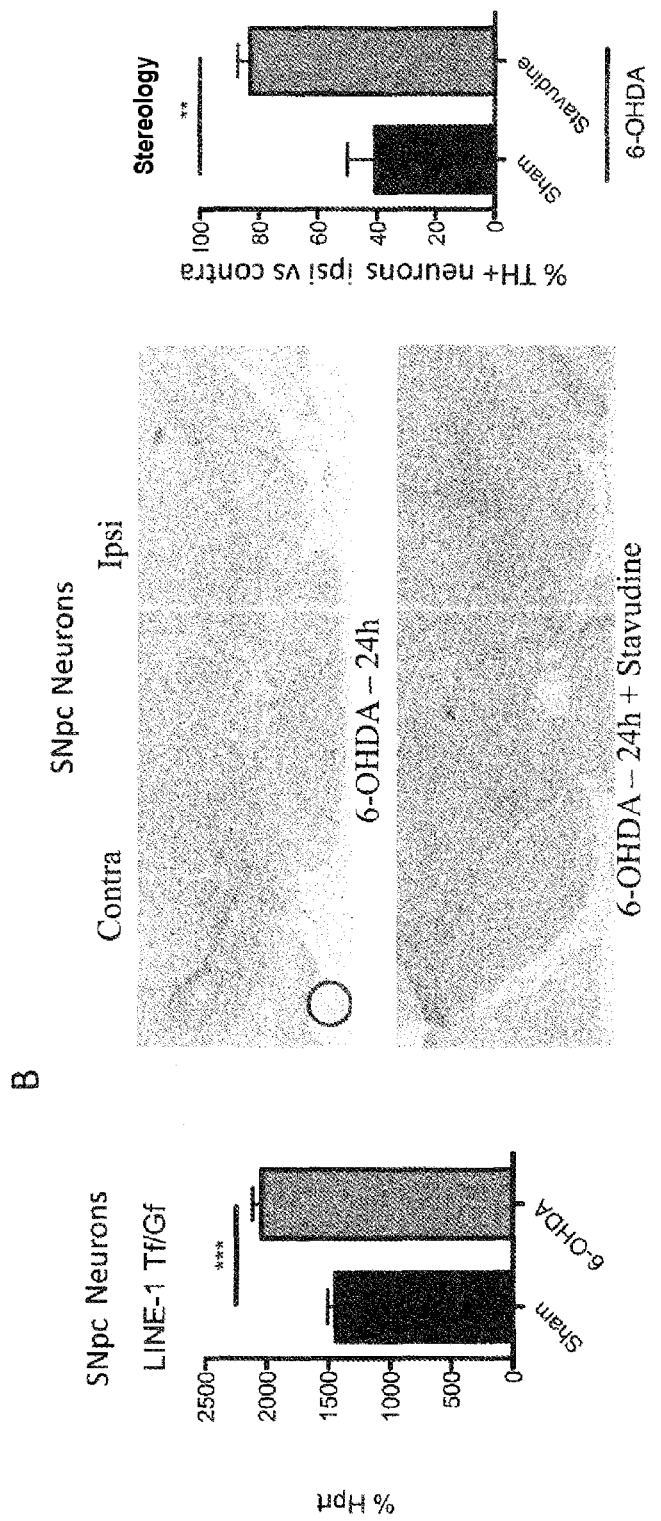

Injection of 6-OHDA into the substantia nigra, which mimics an oxidative stress in vivo, shows an increase in the transcription of LINEs (LINE-1 Tf) in the neurons of the substantia nigra pars compacta (SNpc; FIG. 3A).

The number of TH+ neurons in the substantia nigra pars compacta 24 h after injection of 6-OHDA is higher in the mice treated with Stavudine (FIG. 3B; **$p<0.01$, n=5, Student's test). These results demonstrate that the injection of Stavudine reduces cell death after an oxidative stress in vivo.

REFERENCE LIST

1. Hanks, M., Wurst, W., Anson-Cartwright, L., Auerbach, A. B., and Joyner, A. L. (1995). Rescue of the En-1 mutant phenotype by replacement of En-1 with En-2. Science 269, 679-682.
2. Livak, K. J. and Schmittgen, T. D. (2001). Analysis of relative gene expression using real-time quantitative PCR and the 2(-Delta Delta C(T)) Method 4, 402-408.
3. Marteijn, J. A., Lans, H., Vermeulen, W., and Hoeijmakers, J. H. (2014). Understanding nucleotide excision repair and its roles in cancer and ageing. Nat Rev Mol Cell Biol 15, 465-481.
4. O'Sullivan, R. J., and Karlseder, J. (2012). The great unravelling: chromatin as a modulator of the aging process. Trends Biochem Sci 37, 466-476.
5. Suberbielle, E., Sanchez, P. E., Kravitz, A. V., Wang, X., Ho, K., Eilertson, K., Devidze, N., Kreitzer, A. C., and Mucke, L. (2013). Physiologic brain activity causes DNA double-strand breaks in neurons, with exacerbation by amyloid-beta. Nat Neurosci 16, 613-621.
6. Vijg, J., and Suh, Y. (2013). Genome instability and aging. Annu Rev Physiol 75, 645-668.
7. Höglinger, G. U. et al., 2003. Chronic systemic complex I inhibition induces a hypokinetic multisystem degeneration in rats. *Journal of neurochemistry*, 84(3), pp. 491-502.
8. Xie, Y. et al., 2011. Characterization of L1 retrotransposition with high-throughput dual-luciferase assays. *Nucleic Acids Research*, 39(3), pp. e16e 16.
9. Dalby, B. et al., 2004. Advanced transfection with Lipofectamine 2000 reagent: primary neurons, siRNA, and high-throughput applications. *Methods* (San Diego, Calif.), 33(2), pp. 95-103.

The invention claimed is:

1. A method of treating or preventing a degenerative disease in a subject in need thereof, the method comprising administering a therapeutically effective amount of a reverse transcriptase inhibitor to the subject, said degenerative disease being selected from the group consisting of Parkinson's disease, Alzheimer's disease, Huntington's disease, a degenerative disease affecting eyesight and a degenerative disease affecting hearing.

2. The method of claim 1, wherein the reverse transcriptase inhibitor is a nucleoside inhibitor.

3. The method of claim 2, wherein the degenerative disease is linked to aging or oxidative stress.

4. The method of claim 1, wherein the degenerative disease affecting eyesight is glaucoma.

5. The method of claim 1, wherein the degenerative disease is Parkinson's disease.

6. The method of claim 1, wherein the degenerative disease is Alzheimer's disease.

7. The method of claim 1, wherein the degenerative disease is Huntington's disease.

8. The method of claim 1, wherein the degenerative disease is a degenerative disease affecting eyesight.

9. The method of claim 1, wherein the degenerative disease is a degenerative disease affecting hearing.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: artificial sequence
<220> FEATURE:
<223> OTHER INFORMATION: synthetic primer

<400> SEQUENCE: 1
ctgggaactg ccaaagcaac                                               20

<210> SEQ ID NO 2
<211> LENGTH: 20
<212> TYPE: DNA
<213> ORGANISM: artificial sequence
<220> FEATURE:
<223> OTHER INFORMATION: synthetic primer

<400> SEQUENCE: 2
cctccgttta cctttcgcca                                               20

<210> SEQ ID NO 3
<211> LENGTH: 20
<212> TYPE: DNA
<213> ORGANISM: artificial sequence
<220> FEATURE:
<223> OTHER INFORMATION: synthetic primer

<400> SEQUENCE: 3
ttctgccagg agtctggttc                                               20

<210> SEQ ID NO 4
<211> LENGTH: 20
<212> TYPE: DNA
<213> ORGANISM: artificial sequence
<220> FEATURE:
<223> OTHER INFORMATION: synthetic primer

<400> SEQUENCE: 4
tgagcagacc tggagggtag                                               20

<210> SEQ ID NO 5
<211> LENGTH: 22
<212> TYPE: DNA
<213> ORGANISM: artificial sequence
<220> FEATURE:
<223> OTHER INFORMATION: synthetic primer
```

-continued

```
<400> SEQUENCE: 5
agcaggtgtt ctagtcctgt gg                                              22

<210> SEQ ID NO 6
<211> LENGTH: 22
<212> TYPE: DNA
<213> ORGANISM: artificial seqeunce
<220> FEATURE:
<223> OTHER INFORMATION: synthetic primer

<400> SEQUENCE: 6
acgcagcaac tgacatttct aa                                              22

<210> SEQ ID NO 7
<211> LENGTH: 21
<212> TYPE: DNA
<213> ORGANISM: artificial sequence
<220> FEATURE:
<223> OTHER INFORMATION: synthetic primer

<400> SEQUENCE: 7
tgacgtgccg cctggagaaa c                                               21

<210> SEQ ID NO 8
<211> LENGTH: 21
<212> TYPE: DNA
<213> ORGANISM: artificial sequence
<220> FEATURE:
<223> OTHER INFORMATION: synthetic primer

<400> SEQUENCE: 8
ccggcatcga aggtggaaga g                                               21
```